United States Patent [19]
Lambert, Jr.

[11] Patent Number: 6,013,629
[45] Date of Patent: *Jan. 11, 2000

[54] ANTI-PROTOZOAN METHODS AND MATERIALS

[75] Inventor: Lewis H. Lambert, Jr., Fremont, Calif.

[73] Assignee: XOMA Corporation, Berkeley, Calif.

[*] Notice: This patent is subject to a terminal disclaimer.

[21] Appl. No.: 08/888,876

[22] Filed: Jul. 7, 1997

Related U.S. Application Data

[63] Continuation of application No. 08/273,470, Jul. 11, 1994, Pat. No. 5,646,114.

[51] Int. Cl.$^7$ ............................................. A61K 38/00
[52] U.S. Cl. ........................ 514/12; 514/2; 514/944; 514/937; 424/45; 424/405; 424/DIG. 12
[58] Field of Search .................. 514/2, 12, 944, 514/937; 424/DIG. 12, 45, 405

[56] References Cited

U.S. PATENT DOCUMENTS

| | | |
|---|---|---|
| 5,089,274 | 2/1992 | Marra et al. . |
| 5,171,739 | 12/1992 | Scott . |
| 5,198,541 | 3/1993 | Elsbach et al. . |
| 5,217,956 | 6/1993 | Zasloff et al. ............................ 514/13 |
| 5,234,912 | 8/1993 | Marra et al. . |
| 5,308,834 | 5/1994 | Scott et al. . |
| 5,334,584 | 8/1994 | Scott et al. . |
| 5,348,942 | 9/1994 | Little, II et al. . |
| 5,646,114 | 7/1997 | Lambert, Jr. ............................ 514/12 |

FOREIGN PATENT DOCUMENTS

| | | |
|---|---|---|
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/07895 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |

OTHER PUBLICATIONS

Araujo et al., "In Vitro and In Vivo Activities of the Hydroxynaphthoquinone 566C80 Against the Cyst Form of *Toxoplasma gondii*", *Antimicrobial Agents Chemotherapy*, 36(2):326–330 (Feb. 1992).

Araujo et al., "Remarkable In Vitro and In Viro Activities of the Hydroxynaphthoquinone 566C80 Against Tachyzoites and Tissue Cysts of *Toxoplasma gondii*", *Antimicrobial Agents Chemotherapy*, 35(2):293–299 (Feb. 1991).

Butcher et al., "Heparin Enhances the Interaction of Infective *Leishmania donovani* Promastigotes with Mouse Peritoneal Macrophages", *J. Immunol.*, 148(9):2879–2886 (May 1, 1992).

Butcher et al., "*Leishmania donovani*: Cell–Surface Heparin Receptors of Promastigotes are Recruited from an Internal Pool after Trypsinization", *Experimental Parasitology*, 71:49–59 (1990).

Eliopoulos and Moellering, "Antimicrobial Combinations", in *Antibiotics in Laboratory Medicine*, 3rd ed., pp. 432–492, (Lorian ed., Baltimore, MD) (1991).

Elsbach, "Antibiotics from Within: Antibacterials from Human and Animal Sources", *Trends. Biotech*, 8(1):26–30 (Jan. 1990).

(List continued on next page.)

*Primary Examiner*—Thurman K. Page
*Assistant Examiner*—Lakshmi Channavajjala
*Attorney, Agent, or Firm*—Marshall O'Toole, Gerstein, Murray & Borun

[57] ABSTRACT

The present invention relates to methods for treating protozoan infections comprising administering to a subject suffering from protozoan infection, a bacteriocidal/permeability-inducing (BPI) protein product.

15 Claims, 1 Drawing Sheet

OTHER PUBLICATIONS

Elsbach and Weiss, "Oxygen–Independent Antimicrobial Systems of Phagocytes," in *Inflammation: Basic Principles and Clinical Correlates*, pp. 603–636, (Gallin et al eds., Raven Press, Ltd.) (1992).

Elsbach and Weiss, "Oxygen–Independent Bactericidal Systems of Polymorphonuclear Leukocytes", in *Advances in Inflammation Research*, vol. 2, pp. 95–113 (Weissmann ed., Raven Press, Ltd.) (1981).

Elsbach et al., "Separation and Purification of a Potent Bactericidal/Permability–Increasing Protein and a Closely Associated Phospholipase $A_2$ from Rabbit Polymorphonuclear Leukocytes", *J. Biol. Chem.*, 254(21):11000–11009 (Nov. 10, 1979).

Gabay, "Ubiquitous Natural Antibiotics", *Science*, 264:373–374 (Apr. 15, 1994).

Gazzano–Santoro et al., "High–Affinity Binding of the Bactericidal/Permeability–Increasing Protein and a Recombinant Amino–Terminal Fragment to the Lipid A Region of Lipopolysaccharide", *Infect. Immun.*, 60(11):4754–4761 (Nov. 1992).

Gray et al., "Cloning of the cDNA of a Human Neutrophil Bactericidal Protein", *J. Biol. Chem.*, 264(16):9505–9509 (Jun. 5, 1989).

Hunter et al., "Cytokine mRNA in the Central Nervous System of SCID Mice Infected with *Toxoplasma gondii*: Importance of T–Cell–Independent Regulation of Resistance to *T. gondii*", *Infect. Immun.*, 61(10):4038–4044 (Oct. 1993).

Levy et al., "Antobacterial 15–kDa Protein Isoforms (p15s) are Members of a Novel Family of Leukocyte Proteins", *J. Biol. Chem.*, 268(8):6058–6068 (Mar. 16, 1993).

Mannion et al., "Preferential Binding of the Neutrophil Cytoplasmic Granule–Derived Bactericidal/Permeability–Increasing Protein to Target Bacteria", *J. Clin. Invest.*, 142(8):2807–2812 (Apr. 15, 1989).

Mannion et al., "Separation of Sublethal and Lethal Effects of Polymorphonuclear Leukocytes on *Escherichia coli*", *J. Clin. Invest.*, 86:631–641 (Aug. 1990).

Mannion et al., "Separation of Sublethal and Lethal Effects of the Bactericidal/Permeability Increasing Protein on *Escherichia coli*", *J. Clin. Invest.*, 85:853–860 (Mar. 1990).

Mukhopadhyay et al., "Heparin Binds to *Leishmania donovani* Promastigotes and Inhibits Protein Phosphorylation". *Biochem. J.*, 264:517–525 (1989).

Ooi et al., "A 25–kDa $NH_2$–terminal Fragment Carries All the Antibacterial Activities of the Human Neutrophil 60–kDa Bactericidal/Permeability–Increasing Protein", *J. Biol. Chem.*, 262(31):14891–14894 (1987).

Ooi et al., Endotoxin–neutralizing Properties of the 25 kD N–Terminal Fragment and a Newly Isolated 30 kD C–Terminal Fragment of the 55–60 kD Bactericidal/Permeability–Increasing Protein of Human Neutrophils, *J. Exp. Med.*, 174:649–655 (Sep. 1991).

Ooi et al. "Isolation of Two Isoforms of a Novel 15–kDa Protein from Rabbit Polymorphonuclear Leukocytes that Modulate the Antibacterial Actions of Other Leukocyte Proteins", *J. Biol. Chem.*, 265 (26):15956–15962 (Sep. 15, 1990).

Ortega–Barria et al., "A Novel T. Cruzi Heparin–Binding Protein Promotes Fibroblast Adhesion and Penetration of Engineered Bacteria and Trypanosomes into Mammalian Cells", *Cell*, 67:411–421 (Oct. 18, 1991).

Veld et al., "Effects of the Bactericidal/Permeability–Increasing Protein of Polymorphonuclear Leukocytes on Isolated Bacterial Cytoplasmic Membrane Vesicles", *Infect. Immun.*, 56(5):1203–1208 (May 1988).

Weiss and Olsson, "Cellular and Subcellular Localization of the Bacterial/Permeability–Increasing Protein of Neutrophils", *Blood*, 69(2):652–659 (Feb. 1987).

Weiss et al., "Human Bactericidal/Permeability–Increasing Protein and a Recombiant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.*, 90:1122–1130 (Sep.1992).

Weiss et al., "Resistance of Gram–negative Bacteria to Purified Bactericidal Leukocyte Proteins", *J. Clin. Invest.*, 65:619–628 (Mar. 1980).

Weiss et al., "The Role of Lipopolysaccharides in the Action of the Bactericidal/Permeability–Increasing Neutrophil Protein on the Bacterial Envelope", *J. Immunol.*, 132(6):3109–3115 (Jun. 1984).

Little et al., "Functional Domains of Recombiant Bactericidal/Permeability Increasing Protein (rBPI–23)", *J. Biol. Chem.*, 269(3):1865–1872 (Jan. 21, 1994).

PCT International Preliminary Examination Report for PCT/US95/08624 dated Nov. 7, 1996.

6,013,629

ANTI-PROTOZOAN METHODS AND MATERIALS

This is a Continuation of U.S. application Ser. No. 08/273,470, filed Jul. 11, 1994, U.S. Pat. No. 5,646,114.

BACKGROUND OF THE INVENTION

The present invention relates generally to methods of treating protozoan infections by administration of bactericidal/permeability-increasing (BPI) protein products.

Protozoa are unicellular eukaryotic organisms that can infect and multiply in mammalian hosts. They may utilize more than one type of host, including insect hosts, during their life cycle. Parasitic protozoa account for a significant portion of all infectious diseases worldwide. Although the majority of protozoan infections occur in developing countries, these infections are seen increasingly in industrialized countries among immigrants and immunosuppressed or immunodeficient individuals. Frequently seen parasitic diseases include malaria, caused by the Plasmodia species, toxoplasmosis, caused by *Toxoplasma gondii*, leishmaniasis, caused by Leishmania species, and Chagas' disease (American trypanosomiasis), caused by *Trypanosoma cruzi*. AIDS patients are particularly susceptible to opportunistic protozoan infections such as *Pneumocystis carinii* and *T. gondii*. Treatment of protozoan infections is problematic due to lack of effective chemotherapeutic agents, in some instances, or in other instances because of excessive toxicity of the agents and increasingly widespread resistance to the agents.

Malaria is a major health problem in the tropics, and is caused by four Plasmodium species: *P. falciparum, P. vivax, P. ovale* and *P. malariae*. The developmental cycle of malaria parasites occurs in female mosquitos, which are the vector for spreading disease, and in humans. Female mosquitos inoculate sporozoites into humans during a blood meal. These sporozoites rapidly enter liver cells, where they develop immediately or after some delay into thousands of individual merozoites. In the relapsing malarias, such as *P. vivax* and *P. ovate,* the sporozoites can remain dormant for months to years before entering this proliferative stage. The merozoites rupture from the liver cells and enter the blood stream to invade erythrocytes. These merozoites can either proliferate asexually, or they can differentiate into sexual parasites which then are ingested by the mosquito, where they develop into the infectious sporozoites. After asexual proliferation within the erythrocytes, the merozoites develop through trophozoite forms into the dividing form, the schizont. Each mature schizont contains multiple merozoites which, upon rupture of the infected erythrocyte, are released to invade other erythrocytes and thus continue the cycle.

Clinically, the malaria parasite causes characteristic intermittent fevers and chills, anemia, kidney disease, and brain disease. High levels of parasites in the bloodstream, seen especially in the *P. falciparum* infection, causes serious complications including severe hemolytic anemia, renal failure, and coma. Thus, diagnosis and early treatment of *P. falciparum* is crucial. The drug regimen used for treatment of *P. falciparum* depends on the geographic origin of the infection and the known patterns of drug resistance. Chloroquine resistance is widespread, partial resistance to quinine is seen in many areas, and resistance to the combination of pyrimethamine and sulfadoxine is reported in some areas. Mefloquine is a new anti-malarial that may be effective against chloroquine-resistant *P. falciparum.* Since treatment failure may occur with any drug regimen, the course of the parasitemia must be followed closely. The non-*falciparum* parasites are usually treated with chloroquine or amodiaquine, followed by treatment with primaquine if infection is caused by *P. vivax* or *P. ovale.*

Toxoplasmosis is a common disease among birds and small mammals, especially cats, that is caused by the protozoan *Toxoplasma gondii*. About 20 to 70% of adults in this country have positive serologic tests for Toxoplasma infection, depending on the specific population studied. Human infection usually occurs after exposure to infected cat feces or after consuming undercooked meat. Three forms exist in the life cycle of *T. gondii:* the cyst, the trophozoite and the oocyst. The trophozoite is an intracellular form that proliferates during acute infection. Cysts are forms containing several thousand trophozoites that develop within the host cells. They can be seen in any tissue, but are most commonly found in brain and muscle. Oocysts are forms that exist uniquely in the intestines of cats and are shed by cats. After ingestion, the Toxoplasma are liberated from the cysts or oocysts in the gastrointestinal tract. The trophozoites then disseminate through the blood stream or lymphatic system to infect any nucleated host cell.

The vast majority of people who are infected with Toxoplasma have no apparent clinical symptoms, but a small number develop symptoms including enlarged lymph nodes, fever and fatigue. Congenital infection with Toxoplasma has been estimated to cause 20 to 35% of the cases of retinochoroiditis in children and adults. In the immunodeficient patient, toxoplasmosis can appear as a severe disseminated disease that is rapidly fatal. A combination of pyrimethamine and sulfadiazine has been shown to be effective in inhibiting the replication of trophozoites. However, there are no drugs that will kill trophozoites or eradicate the cyst form. Pregnant women cannot be given pyrimethamine because of its potential to cause birth defects. For patients who cannot tolerate sulfadiazine and pyrimethamine, there are no clearly effective alternatives, although some studies suggest that trimethoprim alone or in combination with sulfa drugs may have some anti-toxoplasma activity.

Leishmaniasis is a protozoan infection caused by the genus Leishmania. This parasite exists in two forms: a mobile flagellated form called a promastigote, and a smaller non-mobile, non-flagellated intracellular form, the amastigote. The promastigotes are found in the gut of the sandfly, which is the vector for spreading disease, while amastigotes infect humans and other vertebrate hosts. In the infected animal, Leishmania are found only in macrophages, where they multiply, rupture the host cell, and infect new cells. When Leishmania are ingested by macrophages, they are enclosed within a phagocytic vacuole, where they proliferate. After the macrophages rupture, the amastigotes are taken up by adjacent cells or are transported to distant sites through the bloodstream or lymphatic system.

Visceral leishmaniasis, or kala-azar disease, is caused by the species *L. donovani*. Primarily affected organs are the liver, spleen, bone marrow and other elements of the reticuloendothelial system, which are enlarged due to the infected macrophages. Other symptoms include fever, weight loss, anemia, and skin lesions. After a few months to a year, the patient becomes emaciated and exhausted. Death is generally due to other concurrent infections. There is also a cutaneous form of leishmaniasis that manifests as ulcerating skin lesions. The drug of choice for treatment of leishmaniasis is pentavalent antimony. Second-line drugs for unresponsive or relapsed patients are pentamidine or amphotericin B. Although orally administered drugs such as rifampin, metronidazole and ketoconazole have been considered for treatment of cutaneous leishmaniasis on the basis of small uncontrolled trials, these drugs are inferior to antimony. Allopurinol analogs are being investigated, but their ultimate usefulness remains to be established.

L. donovani has been found to possess heparin receptors on its cell surface. [Mukhopadhyay et al., Biochem. Journal, 264:517–525 (1989).] These heparin receptors have been localized to the flagellum. [Butcher et al., Experimental Parasitology, 71:49–59 (1990).] It has been shown that protnastigotes and amastigotes of L. donovani bind heparin. Promastigotes in their infective stages bind substantially more heparin than their noninfective counterparts. [Butcher et al., J. Immunol., 148:2879–2886 (1992).] It has also been found that promastigotes in culture produce a cell-associated macromolecule that has characteristics of heparin, indicating that the organism may synthesize heparin or a heparin-like substance. The function of the heparin on the surface of Leishmania may be to facilitate the attachment of parasites to the host phagocytes by serving as a bridge linking the parasite to its host cells, which contain numerous heparin receptors. It has been shown that precoating either parasites or macrophages with heparin augments the interaction of the two cells. Leishmania parasites complete their life cycle within macrophages, which have heparin receptors, but the parasites are killed by neutrophils, which do not bind heparin. Accordingly, the presence of heparin receptors may enhance the likelihood that the parasite will be taken up by a macrophage host cell rather than a neutrophil.

Chagas' disease is an infection caused by Trypanosoma cruzi. It is an incurable multisystemic disease that affects millions of people in Latin America. The prevalence of trypanosomiasis may be as high as 20% of the population in the rural zones of the countries where it is endemic. The parasite exists in three developmental forms: epimastigotes, which multiply extracellularly in the mid-gut of reduviid bugs, the insect vectors for spreading disease; amastigotes, which multiply within mammalian cells; and trypomastigotes, which do not multiply, but transmit infection from the insects to mammals and vice versa. When the insects (reduviid bugs) feed on human blood, the trypomastigotes in their feces penetrate mucous membranes or skin abrasions. The trypomastigotes travel through the blood stream to reach the heart, the gastrointestinal tract and the nervous system, where they invade target cells. After invading the host cell, the trypomastigote transforms into an amastigote, which divides by binary fission. After a number of divisions, amastigotes transform back into trypomastigotes which exit the now ruptured cells, then migrate into neighboring cells or through the blood stream into distant cells. After a period of weeks, the host's immune response suppresses the parasites to very low levels. Small numbers continue to circulate for years.

The acute phase of the disease is characterized by prolonged fever. asthenia, enlarged lymph nodes, edema and hepatosplenomegaly. Afterwards, individuals can remain for many years in a latent or chronic phase. Cardiomyopathy, which occurs in up to 30% of patients, is the most important complication during the chronic phase. Cardiomyopathy is variable in its course; in the acute phase, 10% of the patients die. In the chronic phase, heart disease and heart failure begins in the second to fifth decade and may lead to death. There are two drugs that appear to kill circulating trypanosomes: nifurtimox, a nitrofuran derivative, and benznidazole, a nitroimidazole. T. cruzi strains demonstrate different susceptibilities to these drugs, and both drugs have serious side effects.

Thus, because currently available therapies for protozoan infection are not always effective and may have severe side effects, there remains a need in the art for more effective treatment of protozoan infections.

T. cruzi has been shown to express a unique 60 kD protein on its surface. [Ortega-Barria et al. Cell, 67:411–421 (1991)]. This protein, called penetrin, binds specifically to heparin, heparan sulfate, collagen, and cultured fibroblasts, which are potential host cells of T. cruzi. The ability of T. cruzi trypomastigotes to invade cultured fibroblasts has been shown to be inhibited by penetrin as well as by the glycosaminoglycans heparin and heparan sulfate. The function of penetrin may be to assist the parasites in migrating through the extracellular matrix and to penetrate host cells. Heparin-like sequences and heparan sulfate chains are present on the surface of many potential host cells, including fibroblasts, epithelial cells, glial cells, muscle cells and endothelial cells.

BPI is a protein isolated from the granules of mammalian polymorphonuclear neutrophils (PMNs), which are blood cells essential in the defense against invading microorganisms. Human BPI protein has been isolated from PMNs by acid extraction combined with either ion exchange chromatography [Elsbach, J. Biol. Chem., 254:11000 (1979)] or E. coli affinity chromatography [Weiss, et al., Blood, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., J. Biol. Chem., 264:9505 (1989), incorporated herein by reference.

BPI is a strongly cationic protein. The N-terminal half of BPI accounts for the high net positive charge; the C-terminal half of the molecule has a net charge of −3. [Elsbach and Weiss (1981), supra.) A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., J. Bio. Chem., 262: 14891–14894 (1987)]. In contrast to the N-terminal portion, the C-terminal region of the isolated human BPI protein displays only slightly detectable antibacterial activity against gram-negative organisms. [Ooi et al., J. Exp. Med., 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., Infect. Immun. 60:4754–4761 (1992).

The bactericidal effect of BPI has been reported to be highly specific to gram-negative species, e.g., in Elsbach and Weiss, Inflammation: Basic Principles and Clinical Correlates, eds. Gallin et al., Chapter 30, Raven Press, Ltd. (1992). BPI is commonly thought to be non-toxic for other microorganisms, including yeast, and for eukaryotic cells. Elsbach and Weiss (1992), supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and eukaryotic cells tested at that time. It was also reported that BPI at a concentration of $10^{-6}$ M or 160 μg/ml had no toxic effect, when tested at a pH of either 7.0 or 5.5, on the gram-positive organisms *Staphylococcus aureus* (four strains), *Staphylococcus epidennidis, Streptococcus faecalis, Bacius subtilis, Micrococcus lysodeikticus,* and *Listeria monocytogenes.* BPI at $10^{-6}$ M reportedly had no toxic effect on the fungi *Candida albicans* and *Candida parapsilosis* at Ph 7.0 or 5.5, and was non-toxic to higher eukaryotic cells such as human, rabbit and sheep red blood cells and several human tumor cell lines. See also Elsbach and Weiss, *Advances in Inflammation Research,* ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of $Mg^{++}$ and $Ca^{++}$. Attachment of BPI to the outer membrane of gram-negative bacteria produces rapid permeabilizaton of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms Weiss et al., *J. Clin. Invest.* 65: 619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., *J. Clin. Invest.* 86: 631–641 (1990)). Specific investigation of this possibility has shown that on a molar basis BPI is at least as inhibitory of cytoplasmic membrane vesicle function as polymyxin B (In't Veld et al., *Infection and Immunity* 56: 1203–1208 (1988)) but the exact mechanism as well as the relevance of such vesicles to studies of intact organisms has not yet been elucidated.

There continues to exist a need in the art for new anti-protozoan methods and materials. Products and methods responsive to this need would ideally involve substantially non-toxic compounds available in large quantities by means of synthetic or recombinant methods. Ideal compounds would have anti-protozoan activity when administered or applied as the sole anti-protozoan agent and would also be useful in combinative therapies with other agents.

SUMMARY OF THE INVENTION

The present invention provides methods of treating a subject suffering from a protozoan infection by administration of a composition comprising a BPI protein product. Protozoan infections that may be treated according to the invention include diseases caused by *Toxoplasma gondii,* Leisani species, *Trypanosoma cruzi,* and Plasmodium species.

BPI protein product compositions according to the invention may be administered orally, intravenously, intramuscularly, subcutaneously, aerosolized for pulmonary administration, or as an ointment. BPI protein product compositions may also be administered in conjunction with currently known chemotherapeutic agents for protozoan infections, and may be expected to reduce the amount of chemotherapeutic agent required for therapeutic effectiveness.

According to a further aspect of the invention, a BPI protein product is employed for decontaminating fluids or surfaces contaminated with protozoans. Such methods involve contacting the protozoa with a BPI protein product.

A further aspect of the invention involves use of a BPI protein product for the manufacture of a medicament for treatment of protozoan infection or the use of a BPI protein product in combination with an anti-protozoan agent for the manufacture of a medicament for treatment of protozoan infection.

Numerous additional aspects and advantages of the surprising invention will become apparent to those skilled in the art upon considering the following detailed description of the invention, which describes presently preferred embodiments thereof.

DETAILED DESCRIPTION OF THE INVENTION

Figure 1:
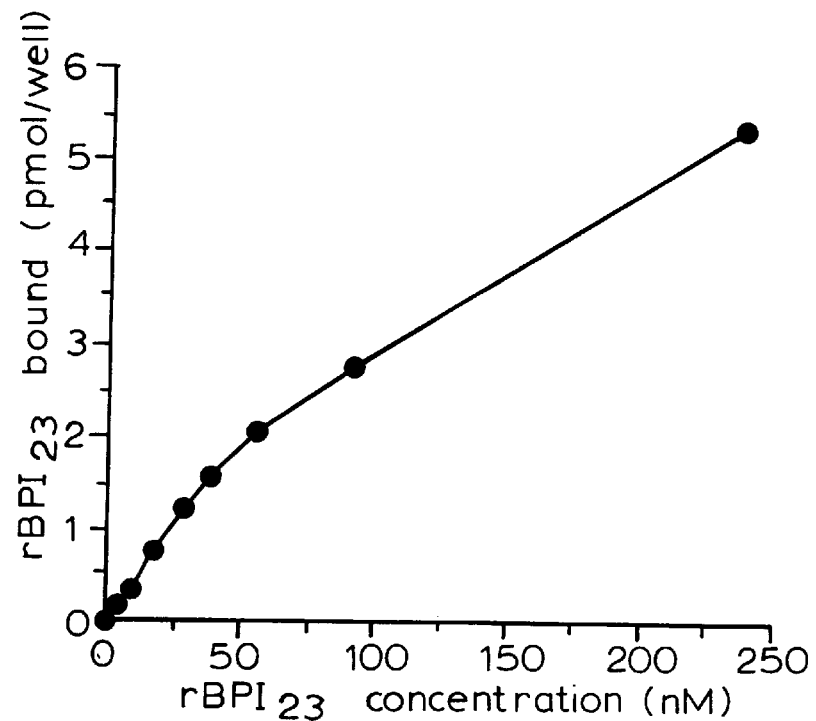
FIGS. 1 and 2 depict the results of an assay of BPI protein product binding to whole (FIG. 1) and lysed (FIG. 2) *Toxoplasma gondii* tachyzoites.

The present invention relates to the surprising discovery that a composition comprising a BPI protein product can be administered to treat subjects suffering from protozoan infections, and provides methods of treating such infections. Protozoan infections that may be treated according to the invention include diseases caused by *Toxoplasma gondii,* Leishmania species, *Trypanosoma cruzi,* and Plasmodium species.

The route of administration for the BPI protein product composition may be topical or systemic, such as orally, intravenously, by intramuscular or subcutaneous injection, aerosolized for pulmonary administration, or formulated as an ointment for topical administration.

The BPI protein product composition may be administered in conjunction with other agents presently known to be effective. BPI protein product may lower the concentration of a non-BPI anti-protozoan agent that is required to eradicate or inhibit replication of the protozoa.

BPI protein product is thought to interact with a variety of host defense elements present in whole blood or serum, including complement, p15 and LBP, and other cells and components of the immune system. Such interactions might result in potentiating and/or synergizing the anti-microbial activities. Because of these interactions, BPI protein products are expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media designed to maximize bacterial growth contain higher than physiological concentrations of magnesium and calcium, inhibitors of BPI protein product antibacterial activity.

Therapeutic effectiveness is based on a successful clinical outcome, and does not require that the anti-protozoan agent or agents kill 100% of the organism involved in the infection. Frequently, reducing organism load by one log (factor of 10) permits the host's own defenses to control the infection. In addition, augmenting an early anti-protozoan effect can be more important than long-term anti-protozoan effect. These early events are a significant and critical part of therapeutic success, because they allow time for host defense mechanisms to activate.

It is also contemplated that the BPI protein product be administered with other products that potentiate the anti-protozoan activity of BPI protein products. For example, serum complement potentiates the gram-negative bactericidal activity of BPI protein products; the combination of BPI protein product and serum complement is provides synergistic bactericidal/growth inhibitory effects. See, e.g., Ooi et al. *J. Biol. Chem.*, 265: 15956 (1990) and levy et al. *J. Biol. Chem.*, 268: 6038–6083 (1993) which address naturally-occurring 15 kD proteins potentiating BPI antibacterial activity. See also co-owned, co-pending U.S. patent application Ser. No. 08/093,201 filed Jul. 14, 1993, and continuation-in-part application U.S. patent application Ser. No. 08/274,303 filed Jul. 11, 1994, now abandoned, which describes methods for potentiating gram-negative bactericidal activity of BPI protein products by administering lipopolysaccharide binding protein (LBP) and LBP protein products. The disclosures of these applications are incorporated by reference herein. LBP protein derivatives and derivative hybrids which lack CD-14 immunostimulatory properties are described in co-owned, co-pending U.S. patent application Ser. No. 08/261,660, filed Jun. 17, 1994, U.S. Pat. No. 5,731,415, as a continuation-in-part of U.S. patent application Ser. No. 08/079,510, filed Jun. 17, 1993, now abandoned, the disclosures of which are incorporated by reference herein.

An advantage provided by the present invention is the ability to treat parasite protozoan infections that are presently considered incurable due to lack of effective chemotherapeutic agents. Another advantage is the ability to treat infection by protozoans that have acquired resistance to the usual agents. A further advantage is the ability to treat protozoan infections for which the currently effective chemotherapeutic agents are highly toxic. Many of the treatment agents are toxic to healthy adults, and cannot be administered to pregnant women. The present invention may also provide quality of life benefits due to, e.g., decreased duration of therapy, reduced stay in intensive care units or overall in the hospital, with the concomitant reduced risk of serious nosocomial (hospital-acquired) infections.

Without being bound by a theory of the invention, it is believed that BPI protein products may have several modes of action. BPI protein product, through its heparin-binding ability, may interfere with the binding of infectious parasite forms to the extracellular matrix and to host cells. BPI protein product may bind to parasites that have heparin-like molecules on their surface. BPI protein product is also postulated to interfere with adhesion between parasites that express heparin-binding receptors and heparan sulfate glycosaminoglycans in the extracellular matrix. Alternatively, BPI protein product may obstruct the action of heparin as a bridge between parasites that express heparin-binding receptors and host cells that express heparin-binding receptors. Alternatively, BPI protein product may bind to LPS-like molecules on the surface of protozoans. In addition, BPI protein product in some cases may act directly on the cytoplasmic membrane of eukaryotic cells.

The invention also provides improved methods of in vitro decontamination of fluids and surfaces contaminated with protozoa comprising contacting the protozoan with a BPI protein product.

A further aspect of the invention involves use of a BPI product for the manufacture of a medicament for treatment of protozoan infection. The medicament may include, in addition to a BPI protein product, other chemotherapeutic agents including anti-protozoan agents. The pharmaceutical composition can optionally comprise a pharmaceutically acceptable diluent, adjuvant or carrier.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; and biologically active polypeptide analogs of BPI protein or fragments or variants thereof, including cysteine-substituted analogs. The BPI protein products administered according to this invention may be generated and/or isolated by any means known in the art. U.S. Pat. No. 5,198,541, the disclosure of which is hereby incorporated by reference, discloses recombinant genes encoding and methods for expression of BPI proteins including recombinant BPI holoprotein, referred to as rBPI$_{50}$ and recombinant fragments of BPI. Co-owned, copending U.S. patent application Ser. No. 07/885,501, now abandoned and a continuation-in-part thereof, U.S. patent application Ser. No. 08/072,063 filed May 19, 1993 U.S. Pat. No. 5,439,807 which are hereby incorporated by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.,* 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, U.S. Pat. No. 5,447,913 (Ammons et al., "Therapeutic Uses Of Bactericidal/Permeability-Increasing Protein Dimer Products" filed Mar. 11, 1994), the disclosure of which is hereby incorporated by reference.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, now abandoned, and a continuation-in-part application thereof U.S. patent application Ser. No. 08/064,693 filed May 19, 1993 U.S. Pat. No. 5,643,570, which are incorporated herein by reference in their entirety and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residue has been replaced by a different amino acid. For example, co-owned, copending U.S. patent application Ser. No. 08/013,801 (Theofan et al., "Stable Bactericidal/Permeability-Increasing Protein Products and Pharmaceutical Compositions Containing the Same," filed Feb. 2, 1993), U.S. Pat. No. 5,420,019, the disclosure of which is incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132, U.S. Pat. No. 5,447,913, (Ammons et al., "Therapeutic Uses Of Bactericidal/ Permeability-Increasing Protein Dimer Products" filed Mar. 11, 1994), the disclosure of which is hereby incorporated by reference.

Other BPI protein products useful according to the methods of the invention are peptides derived from or based on BPI produced by recombinant or synthetic means (BPI-derived peptides), such as those described in co-owned and copending U.S. patent application Ser. No. 08/209,762, filed Mar. 11, 1994, U.S. Pat. No. 5,733,872, which is a continuation-in-part of U.S. patent application Ser. No. 08/183,222, now abandoned, filed Jan. 14, 1994, which is a continuation-in-part of U.S. patent application Ser. No. 08/093,202 filed Jul. 15, 1993), now abandoned, which is a continuation-in-part of U.S. patent application Ser. No. 08/030,644 filed Mar. 12, 1993, U.S. Pat. No. 5,348,942 the disclosures of which are hereby incorporated by reference. Other useful BPI protein products include peptides based on or derived from BPI which are described in co-owned and copending U.S. patent application Ser. No. 08/274,299 filed Jul. 11, 1994 now abandoned and U.S. patent application Ser. No. 08/273,540 filed Jul. 11, 1994, now abandoned, the disclosures of which are hereby incorporated by reference.

Presently preferred BPI protein products include recombinantly-produced N-terminal fragments of BPI, especially those having a molecular weight of approximately between 21 to 25 kD such as $rBPI_{23}$ or $rBPI_{21}$, dimeric forms of these N-terminal fragments. Additionally, preferred BPI protein products include $rBPI_{50}$ (recombinant-produced BPI holoprotein) and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-protozoan agents. A preferred pharmaceutical composition containing BPI protein products comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another preferred pharmaceutical composition containing BPI protein products comprises the BPI protein product at a concentration of 2 mg/ml in 5 mM citrate, 150 mM NaCl, 0.2% poloxamer 188 and 0.002% polysorbate 80. Such preferred combinations are described in co-owned, co-pending, U.S. patent application Ser. No. 08/190,869 filed Feb. 2, 1994 (McGregor et al., "Improved Pharmaceutical Compositions"), U.S. Pat. No. 5,488,034 and U.S. patent application Ser. No. 08/012,360 filed Feb. 2, 1993 (McGregor et al., "Improved Pharmaceutical Composition"), now abandoned, the disclosures of which are incorporated herein by reference.

Other aspects and advantages of the present invention will be understood upon consideration of the following illustrative examples. Example 1 addresses an assay determining the binding of BPI protein product to *Toxoplasma gondii* tachyzoites. Example 2 relates to an in vitro assay for determining the effect of BPI protein product on *T. gondii*. Example 3 addresses the in vivo effect of BPI protein product on *T. gondii* infection in a mouse model. Example 4 relates to an assay determining the binding of BPI protein product to *Leishmania donovani* promastigotes. Example 5 relates to an assay determining the binding of BPI protein product to *Trypanosoma cruzi* trypomastigotes. Example 6 relates to an in vitro assay for determining the effect of BPI protein product on *T. cruzi*.

EXAMPLE 1

Assay to Determine Binding of a BPI Protein Product to *Toxoplasma gondii*

Figure 2:
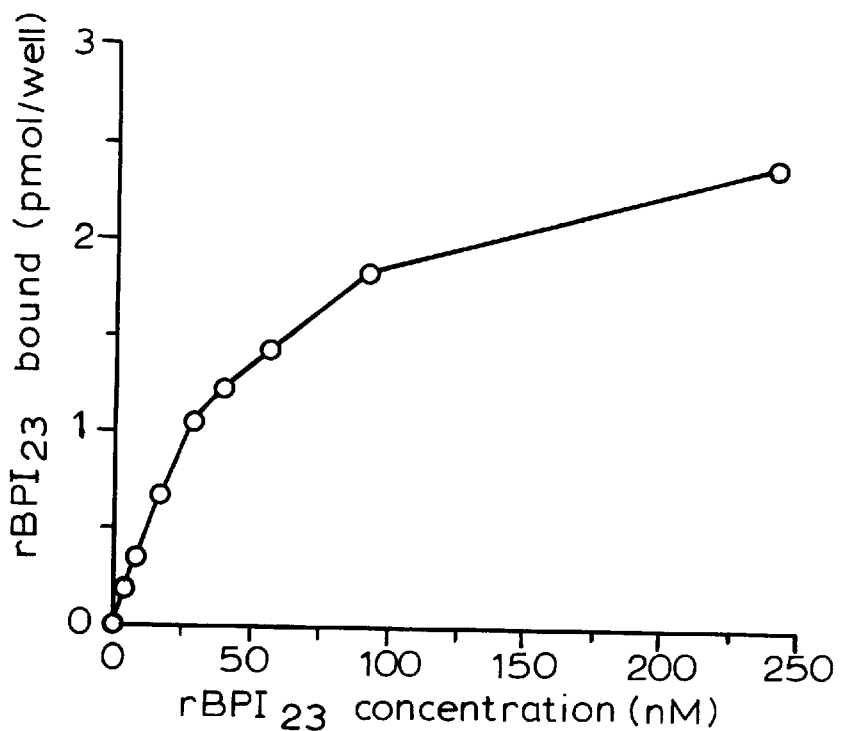

An assay was conducted to determine the binding affinity of a BPI protein product to whole and lysed *Toxoplasma gondii* RH strain tachyzoites. Tachyzoites were obtained as described in Wong et al., *J. Clin. Microbio.*, 5:2950–2959 (1993) at page 2953. Twenty normal Swiss Webster female mice were infected intraperitoneally with *T. gondii* tachyzoites. Two days after infection, ascitic fluid from the mice was harvested into phosphate buffered saline (PBS) containing 10 units/ml heparin at 4° C., filtered through a three micron polycarbonate filter (Nucleopore Corp., Pleasanton, Calif.) to remove white blood cells, and centrifuged at 850× g for 30 minutes. The supernatant was discarded, and TRIS-ammonium chloride was added to the pellet to lyse the red blood cells. The lysed cells were resuspended in PBS and centrifuged. The supernatant was discarded, and the pellet was resuspended with PBS and mixed well. 100 μl of this whole tachyzoite suspension was delivered into Immulon 2 Renovawell strips (Dynatech, Inc., Chantilly, Va.). The remainder of the whole tachyzoite suspension was lysed using a sonicator, and 100 μl of this lysed tachyzoite suspension was delivered into wells. Eight control wells contained no tachyzoite suspension. The wells were placed at 4° C. overnight for saturation. The tachyzoite suspension (whole or lysed) was discarded from the wells and the wells were washed three times with PBS-T (PBS with 0.001% Tween 20). The wells were post-coated with 3% bovine serum albumin (BSA) in 0.1% carbonate-bicarbonate buffer, and incubated for 2 hours at 37° C. The post-coating solution was discarded, and the wells were washed three times with PBS-T. The wells were covered with sterile sealing tape and stored at 4° C. until the assay was performed. For the binding assay, all wells were blocked with 215 μl of D-PBS (Dulbecco's phosphate buffered saline), 0.1% BSA for 1 hour at 37° C. The wells were washed once in D-PBS and then incubated overnight at 4° C. with increasing amounts of $^{125}$I-rBPI$_{23}$ in 100 μl of D-PBS, 0.1% BSA. After five washes with D-PBS, the radioactivity remaining in the wells was counted in an LKB gamma counter. The picomoles (pmol) of rBPI$_{23}$ bound was calculated, and results are displayed in FIGS. 1 and 2 as the mean of six replicate samples. The binding to control wells was taken to represent nonspecific binding; specific binding was defined as the difference between total and nonspecific binding. Nonspecific binding represented between 9 and 40% of total binding. FIG. 1 shows binding of rBPI$_{23}$ to whole tachyzoites; FIG. 2, to lysed tachyzoites. The lysed tachyzoites appear to be almost saturated with rBPI$_{23}$ at a concentration of 100 mM.

EXAMPLE 2

In Vitro Effect of BPI Protein Product on *T. gondii* Tachyzoites and Cysts

The cytotoxic activity of BPI protein product against both the intracellular tachyzoite form and the tissue cyst form of the protozoan *Toxoplasma gondii* is determined in in vitro assays as described in Araujo et al., *Antimicrobial Agents Chemotherapy*, 35: 293–299 (1991). *T. gondii* strains are maintained as chronic infections in mice Swiss Webster. Assays are performed as follows.

For assays using the tachyzoite form, tachyzoites are obtained by inoculating brains of chronically infected mice into the peritoneal cavities of normal mice pretreated with antiserum to gamma interferon, to increase their susceptibility to the infection, as described in Suzuki et al., *J. Parasitol.*, 75:174–176 (1989). Tachyzoites are harvested from intraperitoneal fluid, filtered to remove contaminating peritoneal cells, and counted in a hemacytometer. BPI protein product in formulation buffer is serially diluted 10-fold in RPMI 1640 tissue culture medium (GIBCO, Grand Island, N.Y.) containing 10% human plasma from a donor with no serological evidence of infection with *T. gondii*. Corresponding serial dilutions of formulation buffer alone are also prepared as a control. Human foreskin fibroblasts (HFF) are grown almost to confluence and incubated for 1 hour at 37° C. with tachyzoites at a ratio of two parasites per cell. The monolayers are then washed, medium containing the desired concentrations of BPI protein product is added, and the cultures are incubated for various periods of hours at 37° C. in a 5% $CO_2$ atmosphere. Cultures are pulsed for 8 hours with [$^3$H]uracil, harvested and counted in a liquid scintillation counter. To confirm results obtained with [$^3$H]uracil incorporation, selected HFF cell monolayers are also examined for intracellular replication of tachyzoites by light microscopy after staining with Diff-Quik (American Scientific Products, McGraw Park, Ill.).

For assays using the cyst form, cysts are isolated from brains of CBA/Ca mice chronically infected with strain ME49 and are resuspended in RPMI 1640 tissue culture medium (GIBCO, Grand Island, N.Y.) containing 10% inactivated fetal bovine serum, 100 units/ml of penicillin, 100 μg/ml of streptomycin, 0.25 μg/ml of amphotericin B (Fungizone; all antibiotics and Fungizone from GIBCO, Grand Island, N.Y.) and various concentrations of BPI protein product. (Amphotericin B does not have a significant anti-*T. gondii* effect.) Controls cysts are suspended in medium without BPI protein product. The cyst suspensions are incubated at 37° C. for 24 and 72 hours. After incubation, each cyst suspension is inoculated intraperitoneally into a CBA/Ca mouse pretreated with antiserum to gamma interferon. Mice are monitored for time of death, total mortality, and the presence of tachyzoites in their peritoneal cavities. The blood of surviving mice is tested for the presence of antibodies to *T. gondii* by the Sabin-Feldman dye test, and the brains of surviving mice are examined microscopically for the presence of tissue cysts, as follows. Each brain is ground with mortar and pestle and suspended in 1 ml of phosphate-buffered saline, pH 7.2. Five 20 μl aliquots of brain suspension are each examined by light microscopy, and the number of cysts in each aliquot is counted and averaged.

The assay described in Araujo et al., *Antimicrobial Agents Chemotherapy*, 36:326–330 (1992) is used to determine whether the in vitro sensitivities of cysts vary with their age in vivo. Cysts are isolated from brains of mice infected 1, 2, 3, 4 or 9 months earlier and are resuspended in RPMI culture medium containing 10% fetal bovine serum with or without BPI protein product. The cysts suspensions are incubated at 37° C. in a 5% $CO_2$ atmosphere for 3 or 6 days. After incubation, part of each cyst suspension is stained with a solution of acridine orange and ethidium bromide as described in Huskinson-Mark et al., *J. Infect. Dis.*, 164:170–177 (1991). Viable cysts stain bright green, while cysts affected by treatment variably stain from yellowish green to orange-red and red. The remainder of each cyst suspension is then inoculated intraperitoneally into an SW mouse pretreated with antisera to gamma interferon to enhance its susceptibility to *T. gondii*. The mice are observed for 30 days. The peritoneal fluids of those showing signs of acute toxoplasmosis or those dying during the observation period are examined for the presence of tachyzoites. Surviving animals are bled, their brains are examined for the presence of cysts, and their sera are examined for toxoplasma antibodies using the Sabin-Feldman dye test and an enzyme-linked immunosorbent assay performed with sonically disrupted cysts, as described in Huskinson-Mark, supra.

EXAMPLE 3
In Vivo Effect of BPI Protein Product on *T. gondii* Infection in a Mouse Model The cytotoxic activity of BPI protein product against both the intracellular tachyzoite form and the tissue cyst from of the protozoan *Toxoplasma gondii* is determined in an in vivo mouse model as described in Araujo et al., *Antimicrobial Agents Chemotherapy*, 35: 293–299 (1991).

Outbred Swiss Webster (Simonsen Laboratories, Gilroy, Calif.) and inbred CBA/Ca (Bantin and Kingman Laboratories, Newark, Calif.) female mice, weighing 20 g at the beginning of each experiment, are used. Food and water are available to the animals at all times. Assays are performed as follows.

For assays on the tachyzoite form, tachyzoites are isolated as described in Example 2. Swiss Webster (SW) mice are inoculated intraperitoneally with $3 \times 10^3$ *T. gondii* tachyzoites. At 24 or more hours after inoculation, they are administered varying concentrations of BPI protein product in a single or multiple daily doses, intravenously or intraperitoneally, for 10 or 30 days. Controls are treated similarly with formulation buffer only. Mice are checked twice daily for death, and the presence of parasites in dead animals is determined by microscopic examination of peritoneal fluid. After 30 days, survivors are bled for antibody determination using the Sabin-Feldman dye test, and are euthanized with $CO_2$. The presence of residual infection with *T. gondii* is determined by counting cysts in brain tissue (as described in Example 2) and by subinoculating portions of spleen and liver into other mice. Mice that survive subinoculation with spleen and liver suspensions are bled, and their sera are examined for the presence of antibodies using the Sabin-Feldman dye test.

For assays against the tissue cyst form, CBA/Ca mice are infected intraperitoneally with 20 cysts of *T. gondii* ME49 strain. If untreated. CBA/Ca mice infected with this strain develop a chronic progressive toxoplasmic encephalitis, develop large numbers of cysts in their brains after 3 weeks, and begin to die approximately 6 weeks after the infection. Six weeks after infection, the mice are treated by daily gavage with BPI protein product for 8 weeks. Control mice are treated with formulation buffer only. At 2-week intervals after the initiation of treatment, two or three mice are killed, the entire brains are removed, and the numbers of cysts in the brain suspensions are determined as described above.

The assay described in Araujo et al., *Antimicrobial Agents Chemotherapy*, 36:326–330 (1992) is used to determine the effects of long-term treatment on the numbers of cysts and the inflammatory response in the brain. CBA/Ca mice are infected intraperitoneally with 10 cysts of *T. gondii* ME49 strain and treated daily with BPI protein product administered by gavage, beginning at 5 weeks of infection and continuing for 12 weeks. Control mice, infected similarly, are treated with formulation buffer only. At days 5 and 10 and at weeks 2, 4, 6, 8, 10 and 12 after initiation of treatment, three treated and three control mice are euthanized. Half of each brain is immediately fixed in buffered formalin for histopathology, and the remaining half is processed as described above for microscopic counting of cysts.

The assay described in Araujo (1992), supra, is used to determine in vivo activity of BPI protein product against cysts in the brains of mice infected for prolonged periods of time. SW mice are each infected intraperitoneally with 20 cysts of *T. gondii* ME49 strain. SW mice infected with this strain develop numerous cysts in their brains after 3 to 4 weeks, but unlike in CBA/Ca mice, there is very little inflammatory response and SW mice rarely die from the infection. At 3 and 6 months thereafter, mice are treated with BPI protein product as described above for either 15 or 30 days. AU mice are euthanized at the completion of treatment, and their brains are processed for determination of the numbers of cysts as described above.

An alternative in vivo model (modified from Hunter et al., *Infection and Immunity*, 61:4038–4044 (1993)) may also be used to determine the cytotoxic activity of BPI protein product against *T. gondii*. Swiss Webster adult female mice are maintained in cages with sterlized food and water provided freely. The mice are infected by gavage with 20 purified cysts of the RH strain of *Toxoplasma gondii*, and immediately thereafter the mice are administered BPI protein product intravenously or intraperitoneally. A group of 4 uninfected mice is used as a control. At days 7, 14 and 18 post-infection, groups of 4 infected mice are sacrificed. The mice are anesthetized before sacrifice. The organs are removed: the brain, heart, liver, kidneys, spleen, small intestine and lungs are fixed overnight in a solution of 4% formaldehyde, 70% ethanol, 0.8 N acetic acid and are embedded in paraffin for histopathological analysis. Paraffin sections of 5 $\mu$m are stained with hematoxylin and eosin or used for immunohistochemistry to detect *T. gondii* parasite in tissues by using a peroxidase-antiperoxidase technique with diaminobenzamide as the chromogen. The organs are observed for inflammation, inflammatory lesions, necrosis, and the presence of parasites. Differences in the survival time and the degree of damage seen on histopathology are indicative of the cytotoxic efficacy of a given BPI product treatment regimen.

EXAMPLE 4
Assay to Determine Binding of a BPI Protein Product to *Leishmania donovani*

An assay (modified from Butcher et al., *J. Immunol.*, 148:2879–2886 (1992)] is conducted to determine the binding affinity of a BPI protein product to *Leishmania donovani*. *L. donovani* promastigotes are grown in M199 supplemented with 15% (v/v) FCS and penicillin-streptomycin (1,000 units/ml) as described in Gottlieb et al., *Exp. Parasitol.*, 52:117 (1981). The parasites are harvested by centrifugation, washed, and resuspended at an appropriate concentration in HEPES-buffered saline (HBS), (pH 7.4, supplemented with 5 mM glucose). Log phase promastigotes are harvested on day 3 of culture ($5 \times 10^5$ cells/ml), and stationary phase parasites are harvested on day 7 ($10^8$ cells/ml).

In the binding assay, $2 \times 10^7$ promastigotes are suspended in HBS, pH 7.2, supplemented with 5 mM glucose and varying concentrations of radio-iodinated BPI protein product are added in a final volume of 0.1 ml. Nonspecific binding is determined in the presence of 1 mg/ml unlabeled BPI protein product. The incubation is carried out at 27° C. for 30 min. and is terminated by adding 1 ml of ice cold HBS followed by centrifugation at 20,000× g for 4 min. in a bench-top microcentrifuge. The cell pellets are washed twice with ice cold HBS, resuspended in 0.1 ml of HBS, and counted by liquid scintillation.

EXAMPLE 5
Assay to Determine Binding of a BPI Protein Product to *Trypanosoma cruzi*

An assay (modified from Butcher et al., *J. Immununol.*, 148:2879–2886 (1992)] is conducted to determine the binding affinity of a BPI protein product to *Trypanosoma cruzi*. Trypomastigotes are obtained by infection of cultured Vero cells as described in Prioli et al., *J. Immunol.*, 144:4384–4391 (1990). After harvesting, the parasites are resuspended to the desired concentration in PBS (150 mM NaCl, 20 mM $NaH_2PO_4$, pH 7.2).

In the binding assay, varying concentrations of radioiodinated BPI protein product are added to the trypomastigote suspension in a final volume of 0.1 ml. Nonspecific binding is determined in the presence of 1 mg/ml unlabeled BPI protein product. The incubation is carried out at 27° C. for 30 min. and is terminated by adding 1 ml of ice cold PBS followed by centrifugation at 20,000× g for 4 min. in a bench-top microcentrifuge. The cell pellets are washed twice with ice cold PBS, resuspended in 0.1 ml of HBS, and counted by liquid scintillation.

EXAMPLE 6
In Vitro Effect of BPI Protein Product on Infection by *T. cruzi*

An assay (modified from Ortega-Barria, supra) is conducted to determine the in vitro effect of a BPI protein product on *Trypanosoma cruzi* infection of cultured fibroblasts. Vero fibroblast cells maintained in RPMI 1640 supplemented with heat-inactivated 1% Nu-serum (Collaborative Research, Inc., Bedford, Mass.), penicillin (100 U/ml) and streptomycin (100 mg/ml) are released with trypsin-EDTA (0.5 g trypsin, 0.2 g EDTA in Hanks' balanced salt solution without $Ca^{2+}$ and $Mg^{2+}$) and are plated at approximately $7.5 \times 10^3$ cells/well in a 16 well Lab-Tek chamber slide (Nunc, Inc., Naperville, Ill.). The cells are incubated at 37° C. for 24 hours and are used for infection when they reach 75% confluence. Trypomastigotes are harvested, washed with serum-free RPMI containing 1% BSA and mixed with various concentrations of BPI protein product. After 30 minutes at 37° C. approximately $5 \times 10^5$ parasites in a total volume of 100 $\mu$l is added to each well containing the subconfluent cultures of fibroblasts, and are allowed to interact for 2 hours at 37° C. At the end of the incubation, the fibroblast monolayers are rinsed 3 times with serum-free medium and further incubated in RPMI 1640 containing 1% Nu-serum for 3 days at 37° C. The monolayers are washed, stained with Diff-Quik, and examined under a microscope to estimate the ratio of infected to non-infected Vero cells.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed are:

1. A method of treating protozoan infections comprising the step of administering alone a composition consisting essentially of a therapeutically effective amount of a bactericidal/permeability-increasing (BPI) protein product and a pharmaceutically acceptable diluent, adjuvant or carrier, said BPI protein product being BPI holoprotein, a BPI fragment, a BPI variant, a BPI analog, or a BPI-derived peptide, or dimeric forms thereof, to a subject suffering from a protozoan infection, and wherein protozoa involved in the protozoan infection are susceptible to the BPI protein product.

2. The method of claim 1 wherein the BPI protein product is an N-terminal fragment of BPI or dimeric forms thereof.

3. The method of claim 2 wherein the N-terminal fragment has a molecular weight of approximately between 21 kD and 25 kD.

4. The method of claim 1 wherein the BPI protein product is $rBPI_{23}$ or $rBPI_{21}\Delta cys$ or BPI holoprotein.

5. The method of claim 1 wherein the protozoan species involved in the infection is selected from the group consisting of *Toxoplasma gondii*, Leishmania species, *Trypanosoma cruzi*, and Plasmodium species.

6. The method of claim 5 wherein the protozoan species is *Toxoplasma gondii*.

7. The method of claim 1 wherein the composition is administered orally.

8. The method of claim 1 wherein the composition is administered intravenously, intramuscularly, or subcutaneously.

9. The method of claim 1 wherein the composition is administered as an aerosol.

10. The method of claim 1 wherein the composition is administered as an ointment.

11. A method of treating protozoan infections comprising:
    (a) the step of administering a composition consisting essentially of a therapeutically effective amount of a BPI protein product and a pharmaceutically acceptable diluent, adjuvant or carrier, said BPI protein product being BPI holoprotein, a BPI fragment, a BPI variant, a BPI analog, or a BPI-derived peptide, or dimeric forms thereof, to a subject suffering from a protozoan infection, and wherein protozoa involved in the protozoan infection are susceptible to the BPI protein product; and
    (b) the step of administering a non-BPI anti-protozoan agent.

12. A method of killing or inhibiting growth of a protozoa comprising the step of contacting alone the protozoa with a composition consisting essentially of a bactericidal/permeability-increasing (BPI) protein product in an amount effective to kill or inhibit growth of said protozoa and a pharmaceutically acceptable diluent, adjuvant or carrier, said BPI protein product being BPI holoprotein, a BPI fragment, a BPI variant, a BPI analog, or a BPI-derived peptide, or dimeric forms thereof, and where the protozoa is susceptible to the BPI protein product.

13. A method of killing or inhibiting growth of a protozoa comprising:
    (a) the step of contacting the protozoa with a composition consisting essentially of a BPI protein product in an amount effective to kill or inhibit growth of said protozoa and a pharmaceutically acceptable diluent, adjuvant or carrier, said BPI protein product being BPI holoprotein, a BPI fragment, a BPI variant, a BPI analog, or a BPI-derived peptide, or dimeric forms thereof, and wherein the protozoa is susceptible to the BPI protein product; and
    (b) the step of contacting the protozoa with a non-BPI anti-protozoan agent.

14. The method of claim 11 wherein the composition consisting essentially of a therapeutically effective amount of a BPI protein product and a pharmaceutically acceptable diluent, adjuvant or carrier is administered in conjunction with the non-BPI anti-protozoan agent.

15. The method of claim 13 wherein the composition consisting essentially of a therapeutically effective amount of a BPI protein product and a pharmaceutically acceptable diluent, adjuvant or carrier is contacted with the protozoa in conjunction with the non-BPI anti-protozoan agent.

* * * * *

UNITED STATES PATENT AND TRADEMARK OFFICE
CERTIFICATE OF CORRECTION

PATENT NO. : 6,013,629
DATED : January 11, 2000
INVENTOR(S) : Lewis H. Lambert, Jr.

It is certified that error appears in the above-identified patent and that said Letters Patent is hereby corrected as shown below:

At col. 16, line 39 in claim 12, "where" should be --wherein--.

Signed and Sealed this

Third Day of April, 2001

Attest:

NICHOLAS P. GODICI

*Attesting Officer*  *Acting Director of the United States Patent and Trademark Office*